United States Patent
Schneider et al.

(10) Patent No.: US 11,389,249 B2
(45) Date of Patent: Jul. 19, 2022

(54) LOCALIZED OPTICAL COHERENCE TOMOGRAPHY IMAGES FOR OPHTHALMOLOGICAL SURGICAL PROCEDURES

(71) Applicant: Elbit Systems Ltd., Haifa (IL)

(72) Inventors: Ron Schneider, Haifa (IL); Avi Zeitouni, Haifa (IL)

(73) Assignee: Elbit Systems Ltd., Haifa (IL)

( * ) Notice: Subject to any disclaimer, the term of this patent is extended or adjusted under 35 U.S.C. 154(b) by 652 days.

(21) Appl. No.: 16/099,705

(22) PCT Filed: May 8, 2017

(86) PCT No.: PCT/IL2017/050504
§ 371 (c)(1),
(2) Date: Nov. 8, 2018

(87) PCT Pub. No.: WO2017/195192
PCT Pub. Date: Nov. 16, 2017

(65) Prior Publication Data
US 2019/0183584 A1  Jun. 20, 2019

(30) Foreign Application Priority Data
May 9, 2016  (IL) .......................... 245560

(51) Int. Cl.
*A61B 34/00* (2016.01)
*A61B 34/20* (2016.01)
(Continued)

(52) U.S. Cl.
CPC ............ *A61B 34/20* (2016.02); *A61B 3/0025* (2013.01); *A61B 3/0058* (2013.01); *A61B 3/102* (2013.01);
(Continued)

(58) Field of Classification Search
CPC .. A61B 34/20; A61B 34/0025; A61B 34/0058
See application file for complete search history.

(56) References Cited

U.S. PATENT DOCUMENTS

2012/0184846 A1  7/2012  Izatt et al.
2012/0226150 A1  9/2012  Balicki et al.
(Continued)

FOREIGN PATENT DOCUMENTS

WO  WO 2016/055422  4/2016

OTHER PUBLICATIONS

International Search Report of PCT Application No. PCT/IL2017/050504, dated Sep. 14, 2017.

*Primary Examiner* — Joseph M Santos Rodriguez
(74) *Attorney, Agent, or Firm* — Pearl Cohen Zedek Latzer Baratz LLP

(57) ABSTRACT

Systems and method are provided which enhance ophthalmological surgical procedures. Systems may include camera(s) configured to capture and magnify eye image(s) (possibly stereoscopic), a tissue position and orientation (P&O) tracker configured in to track a P&O of a specified eye tissue, a tool P&O tracker configured to track a P&O of treatment tool(s) and derive a tool tip pointing vector therefrom, a processing unit configured to calculate an intersection between the tool tip pointing vector and the specified eye tissue and to relate spatially optical coherence tomography (OCT) image(s) of the eye tissue to the tool tip location and/or to the intersection, and a display module configured to display the magnified image(s) of the eye tissue with the OCT image(s) associated therewith according to the spatial relation. An OCT imager may be mounted on the tool tip to provide the OCT image(s) in real time.

23 Claims, 8 Drawing Sheets

(51) Int. Cl.
*A61B 3/14* (2006.01)
*A61F 9/007* (2006.01)
*A61B 3/10* (2006.01)
*A61B 3/18* (2006.01)
*A61B 3/00* (2006.01)
*A61B 3/12* (2006.01)
*A61B 90/00* (2016.01)
*A61B 8/00* (2006.01)
*A61B 8/10* (2006.01)
*A61F 9/008* (2006.01)

(52) U.S. Cl.
CPC .............. *A61B 3/1225* (2013.01); *A61B 3/14* (2013.01); *A61B 3/18* (2013.01); *A61F 9/007* (2013.01); *A61B 3/12* (2013.01); *A61B 8/00* (2013.01); *A61B 8/10* (2013.01); *A61B 2034/2057* (2016.02); *A61B 2034/2065* (2016.02); *A61B 2090/3735* (2016.02); *A61F 2009/00851* (2013.01); *A61F 2009/00863* (2013.01)

(56) References Cited

U.S. PATENT DOCUMENTS

2015/0173644 A1    6/2015   Ren et al.
2016/0324593 A1   11/2016   El-Haddad et al.

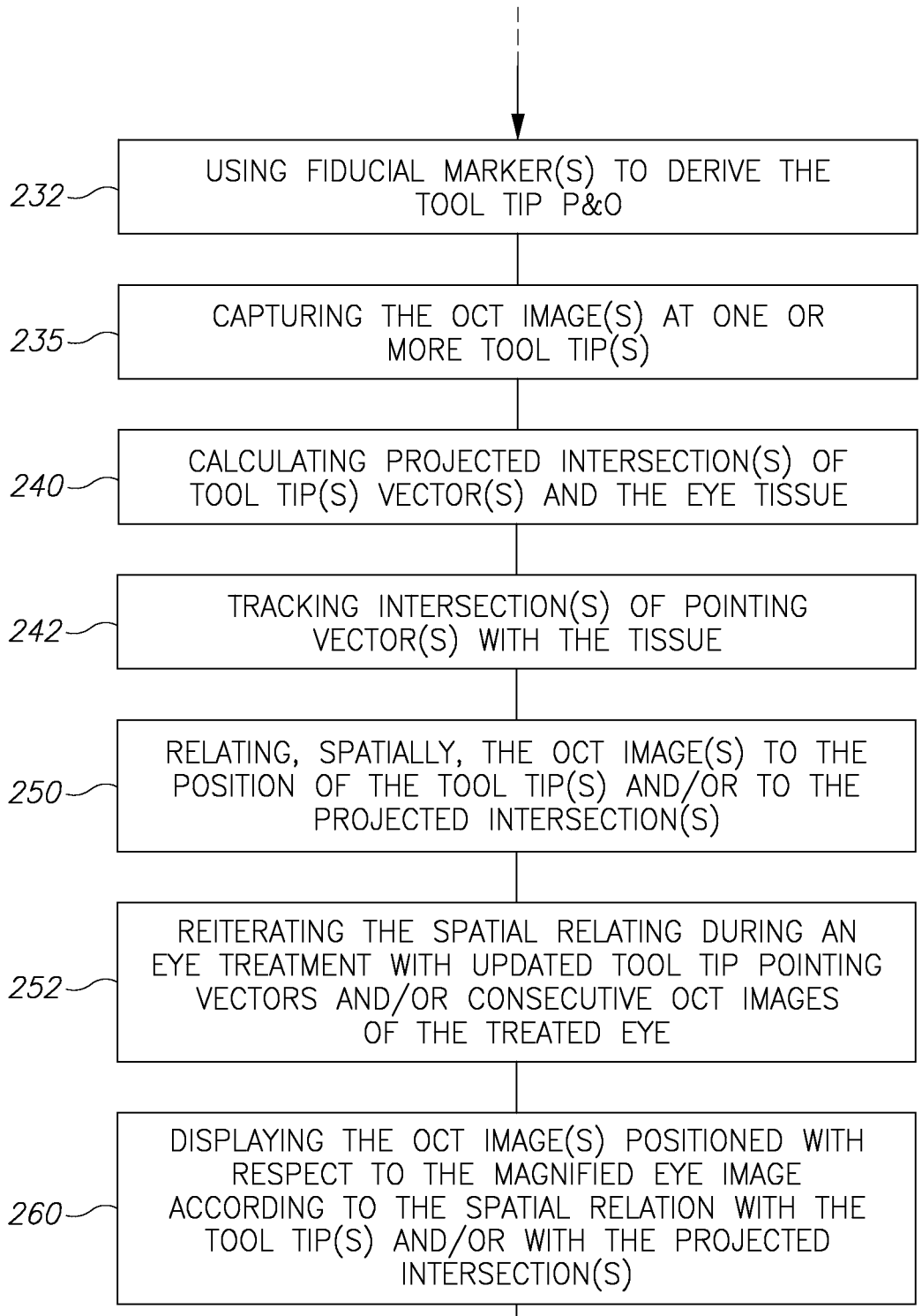
Figure 4 (cont. 1)

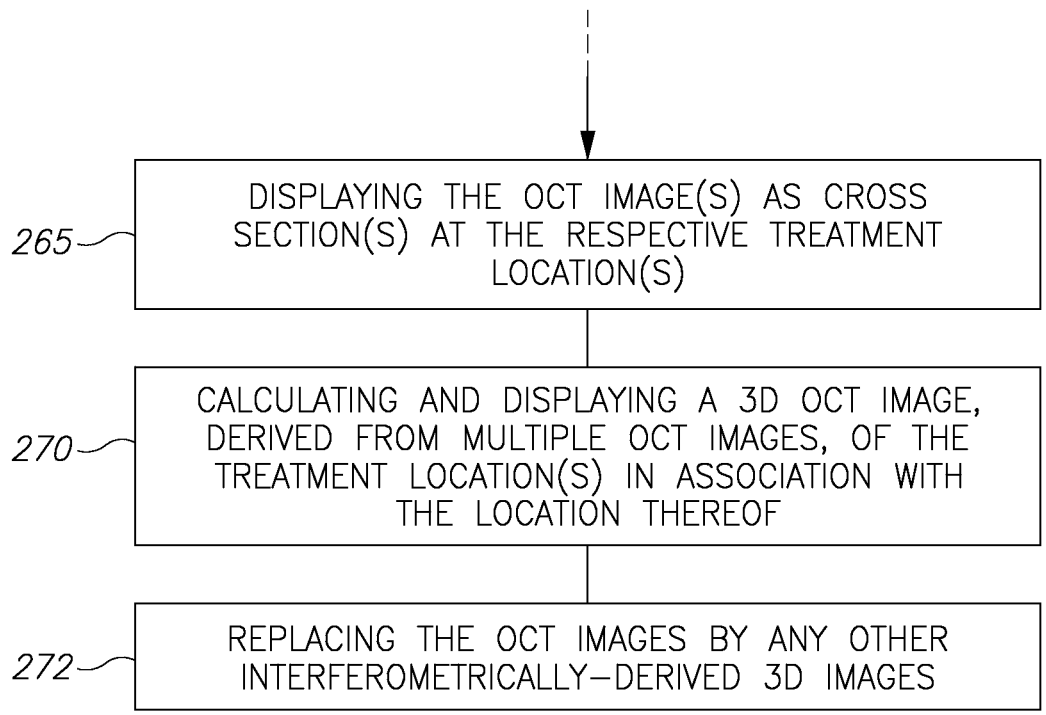
Figure 4 (cont. 2)

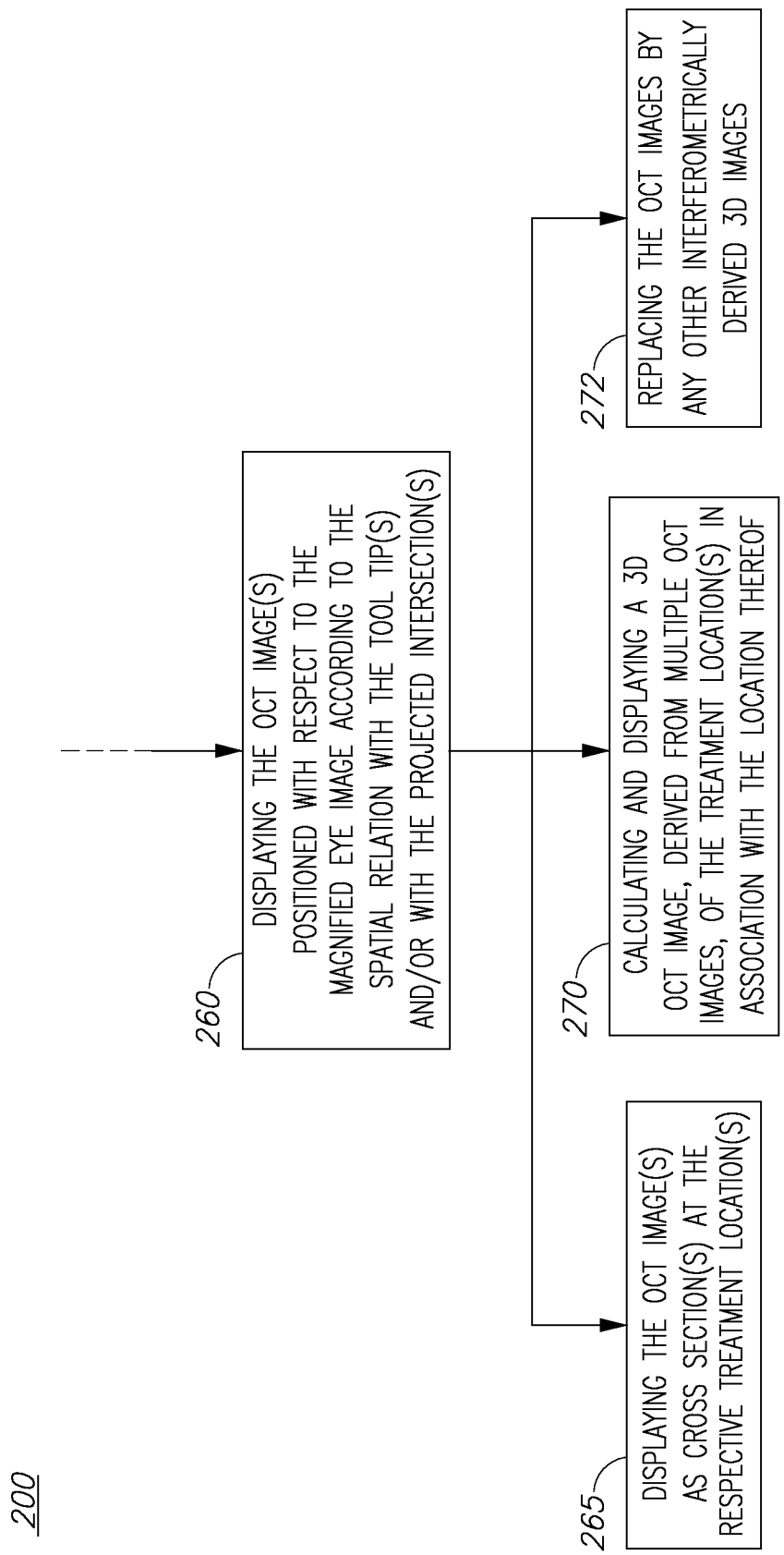
Figure 5 (cont. 1)

LOCALIZED OPTICAL COHERENCE TOMOGRAPHY IMAGES FOR OPHTHALMOLOGICAL SURGICAL PROCEDURES

CROSS-REFERENCE TO RELATED APPLICATIONS

This application is a National Phase Application of PCT International Application No. PCT/IL2017/050504, International Filing Date May 8, 2017, entitled: "LOCALIZED OPTICAL COHERENCE TOMOGRAPHY IMAGES FOR OPHTHALMOLOGICAL SURGICAL PROCEDURES", which was published on Jul.16, 2017 under publication number WO 2017/195192, which claims priority of Israeli Patent Application No., 245560 filed May 9, 2016, all of which are hereby incorporated by reference in their entireties.

BACKGROUND OF THE INVENTION

1. Technical Field

The present invention relates to the field of medical imaging, and more particularly, to ophthalmological magnified intra-operative visualization combined with OCT (optical coherence tomography) imaging.

2. Discussion of Related Art

Retina surgeries are common procedures in ophthalmology. The surgeries are being made using stereoscopic microscope and very thin and small surgical tools. During the procedure the surgeon is compelled to cut or avoid cutting very narrow transparent tissues with accuracy of micrometers or tens of micrometers. Damage to tissues in the eye can cause complications during the surgery, long period of patient recovery time, decreased performance of the procedure and even the need for repeated surgeries. In other cases, in which the surgeon cannot make an accurate incision based on vision through the microscope, the performance of the surgical procedure can be degraded.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a system for ophthalmological surgical procedures, the system comprising at least one camera configured to capture and magnify at least one image of a specified eye tissue, a tissue position and orientation (P&O) tracker configured to track a P&O of the specified eye tissue, a tool P&O tracker configured to track a P&O of at least one tool and derive a tool tip pointing vector therefrom, a processing unit configured to calculate an intersection between the tool tip pointing vector and the specified eye tissue and to relate spatially at least one optical coherence tomography (OCT) image of the specified eye tissue to the calculated intersection, and a display module configured to display the at least one magnified image of the specified eye tissue with the at least one OCT image associated therewith according to the spatial relation.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Figure 1:
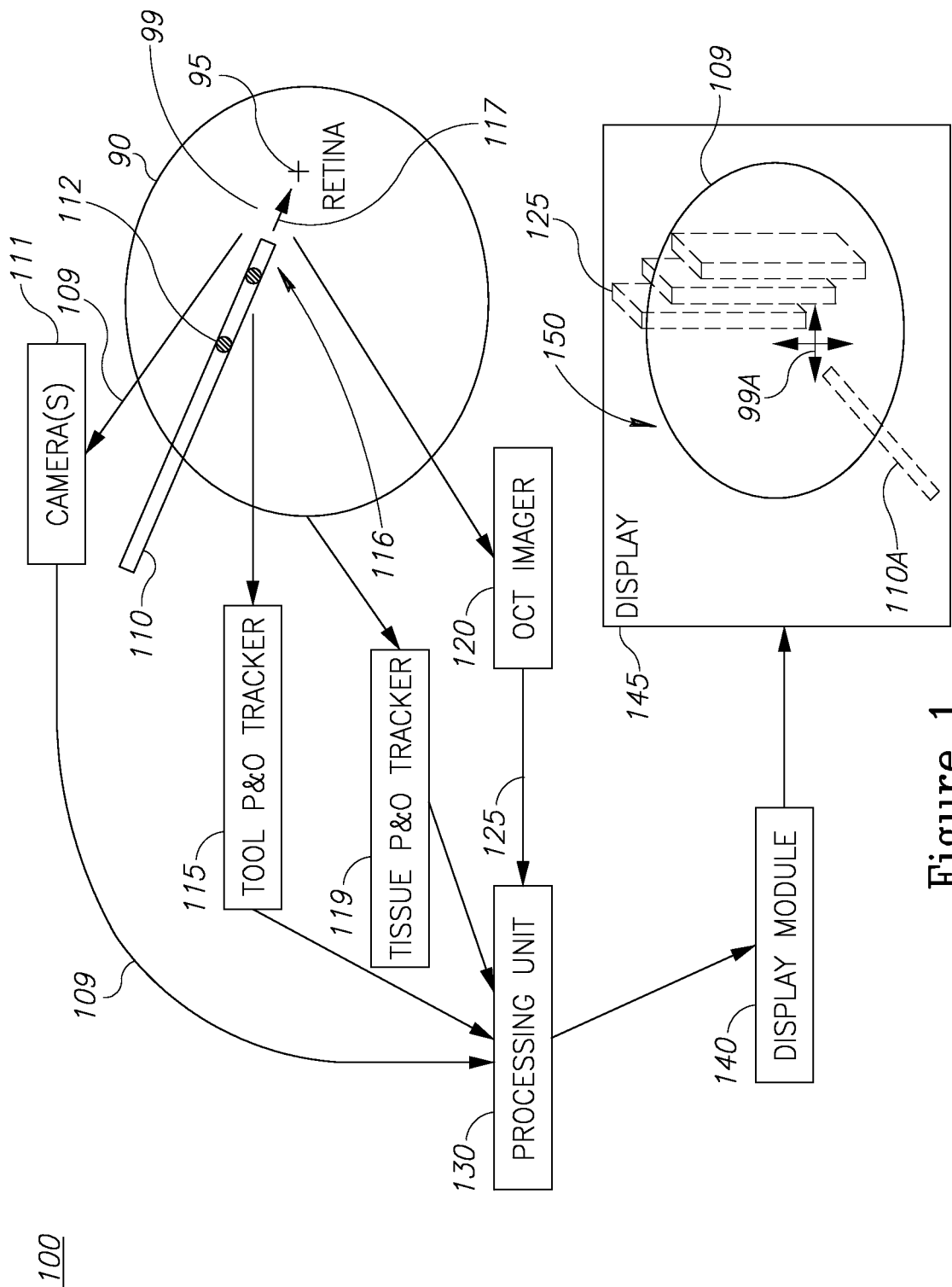
FIG. 1 is a high level schematic block diagram of a system for ophthalmological surgical procedures, according to some embodiments of the invention.

Prior to the detailed description being set forth, it may be helpful to set forth definitions of certain terms that will be used hereinafter.

The term "pointing vector" as used in this application refers to an indicator of position and orientation (P&O) in a three dimensional space, such as a vector denoting a P&O of a tool tip (i.e., extends therefrom along its length). The pointing vector may be defined by any means, such as by a position and an orientation (P&O) of a treatment tool or any other tool or utensil, or by a geometric definition, e.g., by spatial angles or an indication on a 3D (three dimensional) image or on a GUI (graphical user interface). In case of a tool tip pointing vector, the pointing vector may be derived as the center vector of the tool assuming cylindrical symmetry and/or based on two distant points along the tool tip. The term "intersection" as used in this application refers to a location in which a pointing vector coincides with a surface defined by a treated tissue. It is noted that the location may be a point, a line and/or an area on the surface and may optionally be located above or below the surface according to requirements of the respective procedure (e.g., medical procedure). The term "projection intersection" as used in this application refers to a location in which a tool is estimated to coincide with a treated tissue. For example, the projection intersection may be defined as being equal to the intersection of a tool pointing vector (i.e., a vector indicating the P&O of the tool) with a surface of the treated tissue. Here too, the location may be a point, a line and/or an area on the surface and may optionally be located above or below the surface according to requirements of the respective procedure (e.g., medical procedure).

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways. Also, it is to be understood that the phraseology and terminology employed herein is for the purpose of description and should not be regarded as limiting.

Systems and method are provided which enhance ophthalmological surgical procedures. Systems may include camera(s) configured to capture and magnify eye image(s) (possibly stereoscopic), an eye tissue position and orientation (P&O) tracker configured to track a P&O of a treated eye tissue, a tool P&O tracker configured to track a P&O of treatment tool(s) and derive a tool tip pointing vector therefrom, a processing unit configured to calculate an intersection between the tool tip pointing vector and the specified eye tissue (and/or to calculated a projected intersection between the tool tip and the specified eye tissue) and to relate spatially optical coherence tomography (OCT) image(s) of the treated eye to the tool tip and/or the intersection, and a display module configured to display the magnified image(s) of the treated eye with the OCT image(s) associated therewith according to the spatial relation. An OCT imager may be mounted on the tool tip to provide the OCT image(s), e.g., in real time. It is explicitly noted that in case of ophthalmological procedures, the intersection may be defined as the projected intersection of a tool with the retina, and the systems and methods may be configured to prevent actual contact of the tool tip with the retina, e.g., by alarming when the distance to the projected intersection falls below a specified threshold.

FIG. 1 is a high level schematic block diagram of a system 100 for ophthalmological surgical procedures, according to some embodiments of the invention. System 100 comprises at least one camera 111 configured to capture and magnify at least one eye image 109, an eye tissue position and orientation (P&O) tracker 119 (in addition and/or enhancing a gaze tracker, which is not shown here) configured to track a P&O of a treated eye tissue 90, a tool P&O tracker 115 configured to track a P&O of at least one tool 110 (for example, a mechanical or an electro-optical, e.g., laser, tool) and derive a tool tip pointing vector 117 (indicating the direction of tool tip 116 with respect to any selected reference frame, e.g., an external reference frame such as an operating room or an internal reference frame such as the eye) therefrom, a processing unit 130 configured to calculate an intersection 99 between the tool tip pointing vector 117 and a specified part 95 of the eye tissue (e.g., the retina or part thereof) (and/or to calculated a projected intersection between the tool tip and the specified eye tissue) and to relate spatially at least one optical coherence tomography (OCT) image 125 of treated eye 90, and specifically of treated eye tissue 95, to at least one of a tool tip (116) location and intersection 99, and a display module 140 configured to display (on display 145) the at least one magnified image 109 of the treated eye 90 with at least one OCT image 125 associated therewith according to the spatial relation. In a displayed composite image 150, imaged tool (tip) 110A may be displayed with respect to imaged intersection 99A (on eye image 109) and OCT image(s) 125 may be displayed in any one of various spatial relations such as at intersection 99A; at a current or at an expected intersection of tool tip 116 and a tissue such as the retina of the treated eye; in a common plane with tool tip 116 and/or as a three dimensional reconstruction of a retinal region, e.g., at intersection 99 or beyond. The spatial relation may also comprise marking intersection 99 in image 150; indicating the cross section that corresponds to at least one OCT image 125; possibly distorting and registering OCT image(s) 125 according to tool tip pointing vector 117 (e.g., in continuation thereof); and/or indicating, on OCT image(s) 125, a penetration of tool tip 116 into the respective cross section of treated tissue 95 and enable measurement e.g., of (depth) distance to a certain type of tissue 95 (e.g., evaluating a distance left to the retina within eye tissue 95).

Processing unit 130 may be configured to carry out the spatial relating by estimating a distance and a spatial angle of tool tip 116 from at least one plane of at least one OCT image 125. For example, processing unit 130 may be configured to implement various image processing procedures to further enhance and fine tune composite image 150. For example, processing unit 130 may identify tool tip 116 and/or the retina in image 109 and use stereo imaging to provide rough information on the distance between tool tip 116 and the retina. Alternatively or complementarily, processing unit 130 may be configured to compare multiple, possibly previously taken images of the eye (for example fundus images) to provide information on the location of tool tip 116 with respect to tissue 95 (such as the retina).

Processing unit 130 and display module 140 may be further configured, respectively, to calculate and display a 3D (three dimensional) OCT image (not shown), derived from a plurality of OCT images 125, of specified eye tissue 95 at intersection 99.

Figure 2:
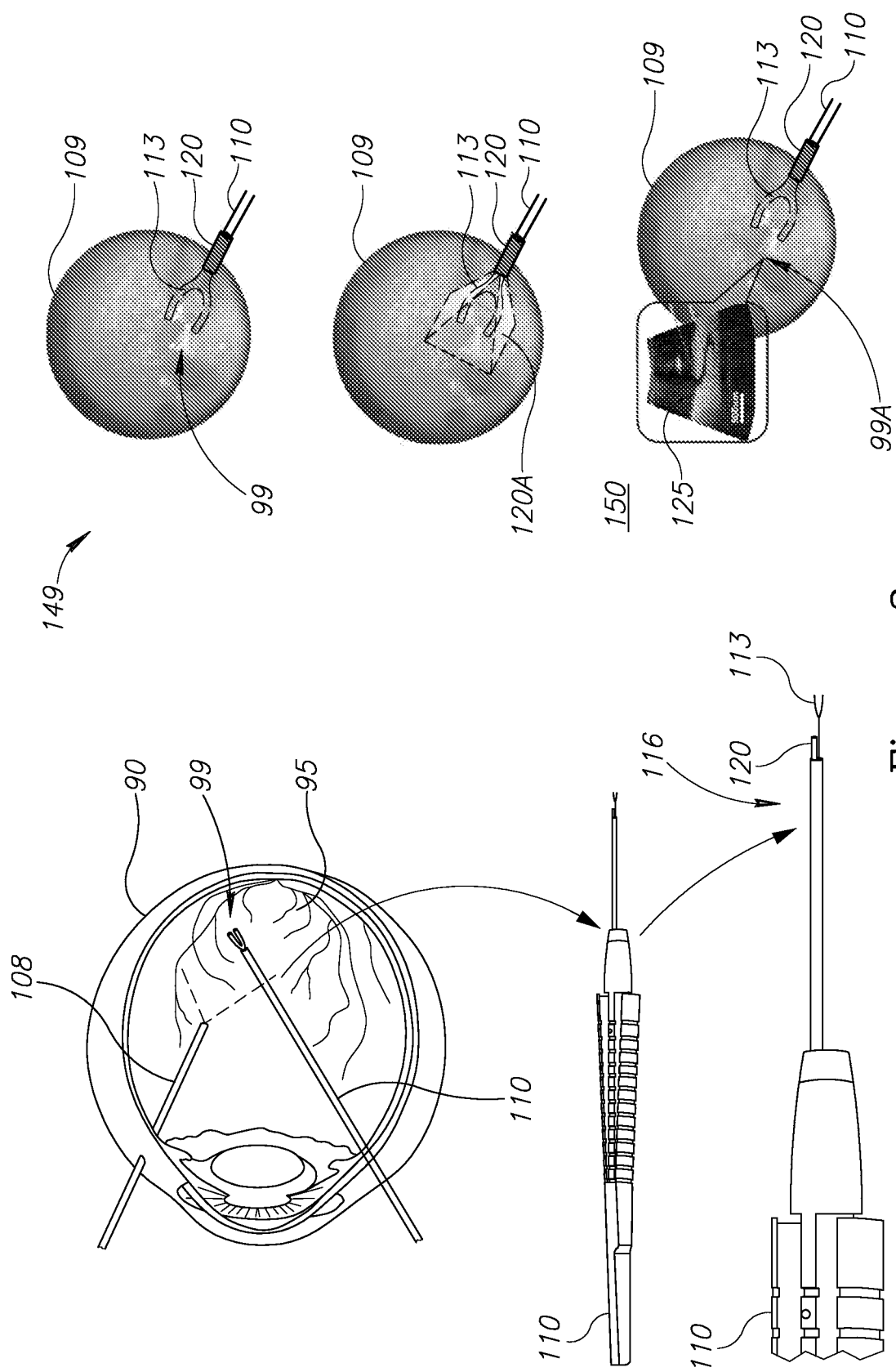
FIG. 2 presents high level schematic illustrations of ophthalmological surgical procedures with the system, according to some embodiments of the invention.

OCT image(s) 125, which may be e.g., OCT retinal images, may be captured by an OCT imager 120 that can be an external OCT imager and/or an OCT imager which is mounted on the tip of tool 110 (e.g., fiber-based, possibly disposable, see FIG. 2). At least one OCT image 125 may be captured prior to and/or during a treatment of the eye and may be received from at least one OCT image source 120 which is independent of tool tip 116 and/or is mounted on tool tip 116. At least one OCT image 125 may comprise a plurality of consecutive OCT images 125 captured during an eye treatment, with processing unit 130 being further configured to carry out the spatial relating repeatedly with respect to consecutive OCT images 125, and with display module 140 being configured to update displayed OCT image(s) 125 themselves and their display position, according to the repeated spatial relating. Processing unit 130 may be configured to utilize data from the OCT images to estimate accurately the distance between OCT imager 120, and possibly tool tip 116 when the former is mounted on the latter, and treated tissue 95 (such as the retina or part thereof). This information may be used by processing unit 130 and system 100 to increase the accuracy of the prediction of the interception of tool tip 116 and treated tissue 95, and alert to prevent accidental damage of the retina.

Any of the following image fusion alternatives may be generated by system 100. OCT images 125 may be registered to the intersection of tool tip 116 and tissue 95, possibly enhanced by additional data, e.g., from angiography, fluorescence imaging etc. OCT images 125 that are captured prior to the actual procedure may be associated with respective locations in the eye. Real-time OCT images 125 may be captured during the procedure from within the eye, possibly in association with tool tip 116. Real-time OCT images 125 may be captured during the procedure by an external OCT imaging device operating outside the eye. Any real-time OCT images 125 may be displayed in association with eye image 109.

Tissue P&O tracker 119 may comprise a stereoscopic camera, operating in the visible or infrared waveband spectrums, specified eye tissue 95 may be a retina or part thereof and OCT image(s) 125 may be OCT retinal image.

Tool 110 may comprise at least one fiducial marker 112 used for the derivation of tool tip pointing vector 117. Camera 111 may provide microscopic images of treatment area 95. Tissue P&O tracker 119 may be integrated in camera 111, especially when the latter is configured as a 3D camera (e.g., a stereoscopic camera). Alternatively or complementarily, tissue P&O tracker 119 may comprise a time-of-flight sensor (implementing gated imaging) and/or operate using structured light to retrieve 3D features. Tissue P&O tracker 119 may be configured to identify specific eye features and/or fiducials that are placed near or on the eye (e.g., on the conjunctiva) to enhance the detection of the relative positions (registration) of OCT image(s) 125 and eye tissue 95.

Tool P&O tracker 115 may apply any of various methods for tracking tool 110 and particularly tool tip 116, such as, but not limited to, the following methods. Tool P&O tracker 115 may be coupled (e.g., optically, electromagnetically, by ultrasound, etc. with corresponding markers 112 on tool 110. Tool P&O tracker 115 may be integrated in camera 111, especially when the latter is configured as a 3D camera, and use e.g., passive or active markers on tool 110 which are identifiable on image 109. Tool P&O tracker 115 may configured to track a (distorted) shape of tool, based e.g., on preliminary learning stages and/or database information. Tool P&O tracker 115 may comprise an electromagnetic tracker with corresponding markers (e.g., coils, Hall effect sensors) on tool 110, or an ultrasonic tracker with corresponding transducers as markers 112. Tool P&O tracker 115 and markers 112 may comprise an inertial navigation system providing information regarding the linear and rotational accelerations of tool 110. Markers 112 on tool 110 may be position within the eye or outside the eye and be used for the derivation of the tool's P&O.

FIG. 2 presents high level schematic illustrations of ophthalmological surgical procedures with system 100, according to some embodiments of the invention. An illumination tool 108 and treatment tool 110 may be introduced through the sclera of treated eye 90 to approach treatment area 95 such as the retina. Tool 110 may comprise e.g., tweezers 113 at tip 116 and OCT imager 120 may be mounted on tool tip 116, e.g., just behind tweezers 113. Alternatively or complementarily, OCT imager 120 may be positioned outside the eye. Schematic images 149 are presented to illustrate tool tip 116 with tweezers 113 approaching the retina within eye image 109, with calculated intersection 99 indicated schematically (top right), and with a schematic illustration of the field of view of mounted OCT imager 120 (middle right). Composite image 150 illustrates schematically, in a non-limiting manner, the spatial association of OCT image(s) 125 with displayed intersection 99A (bottom right).

System 100 or parts thereof may be incorporated in a head mounted display (HMD) of any kind, e.g., display 145 may be on the HMD, and possibly any of display module 140 trackers 115, 119 and processing unit 130 may be part of the HMD. Alternatively or complementarily, the HMD may comprise a communication module that communicates with components which are not integrated in the HMD, e.g., with display module 140 or processing unit 130.

Figure 3:
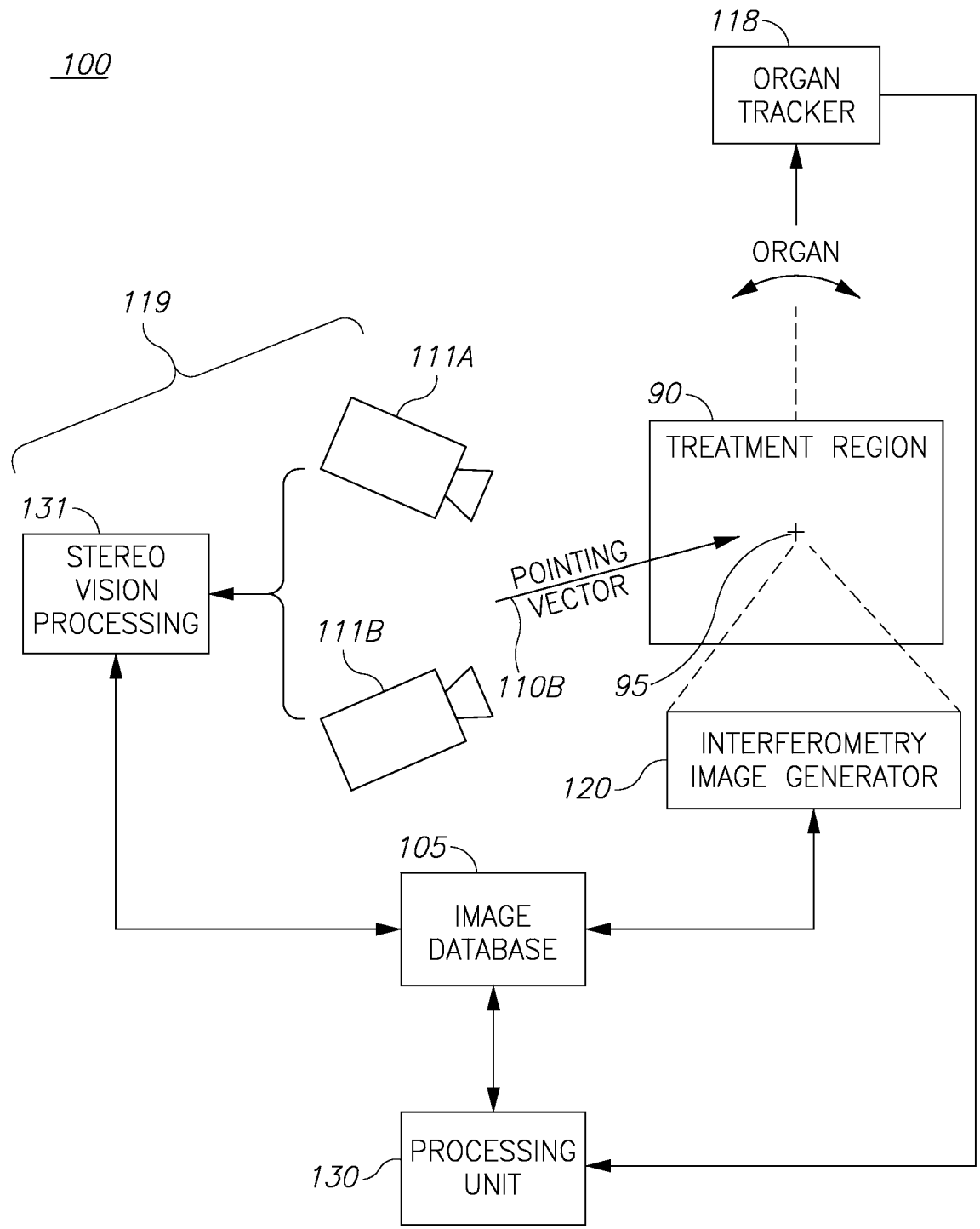
FIG. 3 is a high level schematic block diagram of a system 100, according to some embodiments of the invention.

FIG. 3 is a high level schematic block diagram of a system 100, according to some embodiments of the invention. System 100 illustrates schematically several aspects which may be implemented separately or in combination, namely the tracking of an organ on which the treated tissue is located, the use of interferometry image generator(s) 120 as described below, the use of stereo vision to track the eye and the definition and reference to a pointing vector and not necessarily to a tool tip. Any of these aspects may be implemented in any of the embodiments.

In certain embodiments, applicable to any of systems 100 described herein, an organ tracker 118 may be used in order to track movements of a patient's organ that supports treatment regions, such as the eye or head in ophthalmological procedures, a respective organ in skin treatments, the skull or head in brain surgeries etc. Organ tracker 118 measurements may be incorporated into the calculation of the intersection of tool 110 and/or pointing vector 110B with treated region 90, and to the respective displaying of the 3D imaging—by processing unit 130. The respective organ may be tracked using various methods, such as using fiducials and stereo vision, as described with respect to the eye as a non-limiting example. Organ tracking may be especially important when imager 120 is not physically associated with tool tip 110, and may be accompanies by capturing multiple OCT images of the surroundings of the treatment location.

System 100 may be configured to associate images of treatment region 90, captured by one or more interferometric imager 120 such as OCT imager 120 and/or an ultrasound imager, confocal microscopy, a gated imager (utilizing time of flight measurements of e.g., femtosecond laser illumination to yield three dimensional data and images) and/or any other imager that utilizes interferometric methods to derive 3D image(s) (i.e., images with surface as well as depth information relating to the tissue) of treatment region 90 and/or treated location 95—with an intersection of pointing vector 110B with the treated tissue. For example, system 100 may be used to treat the eye, skin or brain tumors, in back-related procedures, in endoscopic and laparoscopic procedures, and in other procedures, depending on the depth of imaging of the selected interferometric imaging method.

In certain embodiments, applicable to any of systems 100 described herein, eye tracker 119 may be embodied, replaced or enhanced by a stereoscopic vision unit comprising at least two cameras 111A, 111B (possibly at least one of which also providing images of the eye) and a corresponding stereovision processing unit 131 that are configured to provide eye position (and orientation) data to processing unit 130. In such embodiments, fiducials may not be needed to track the eye, as OCT images 125 may be associated with the stereoscopic image(s) of the eye. Clearly in other types of procedures stereoscopic tracking may be likewise applied to the relevant tissue or organ.

Figure 4:
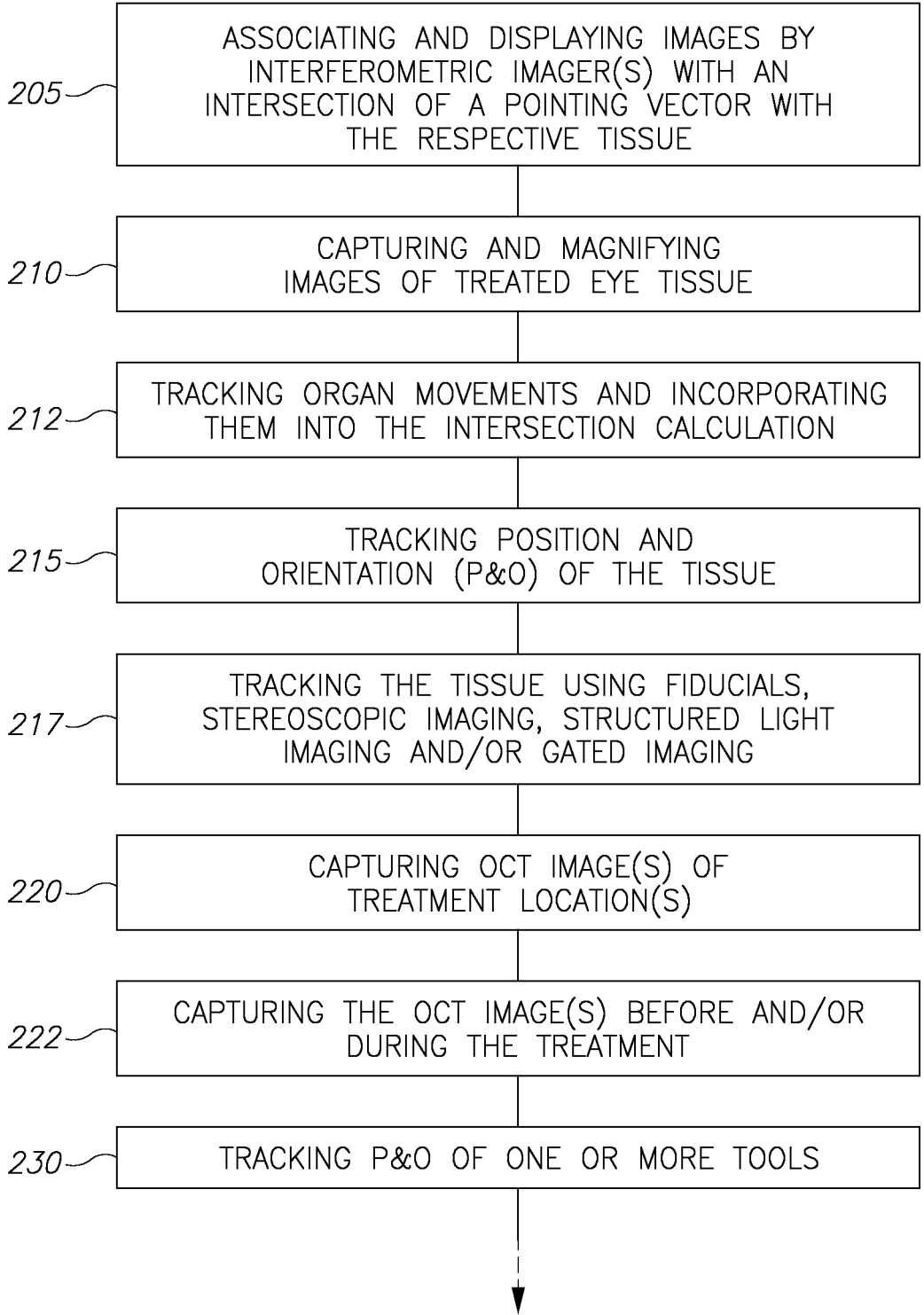
FIGS. 4 and 5 are high level flowcharts illustrating a method of enhancing ophthalmological surgical procedures, according to some embodiments of the invention.
Figure 5:
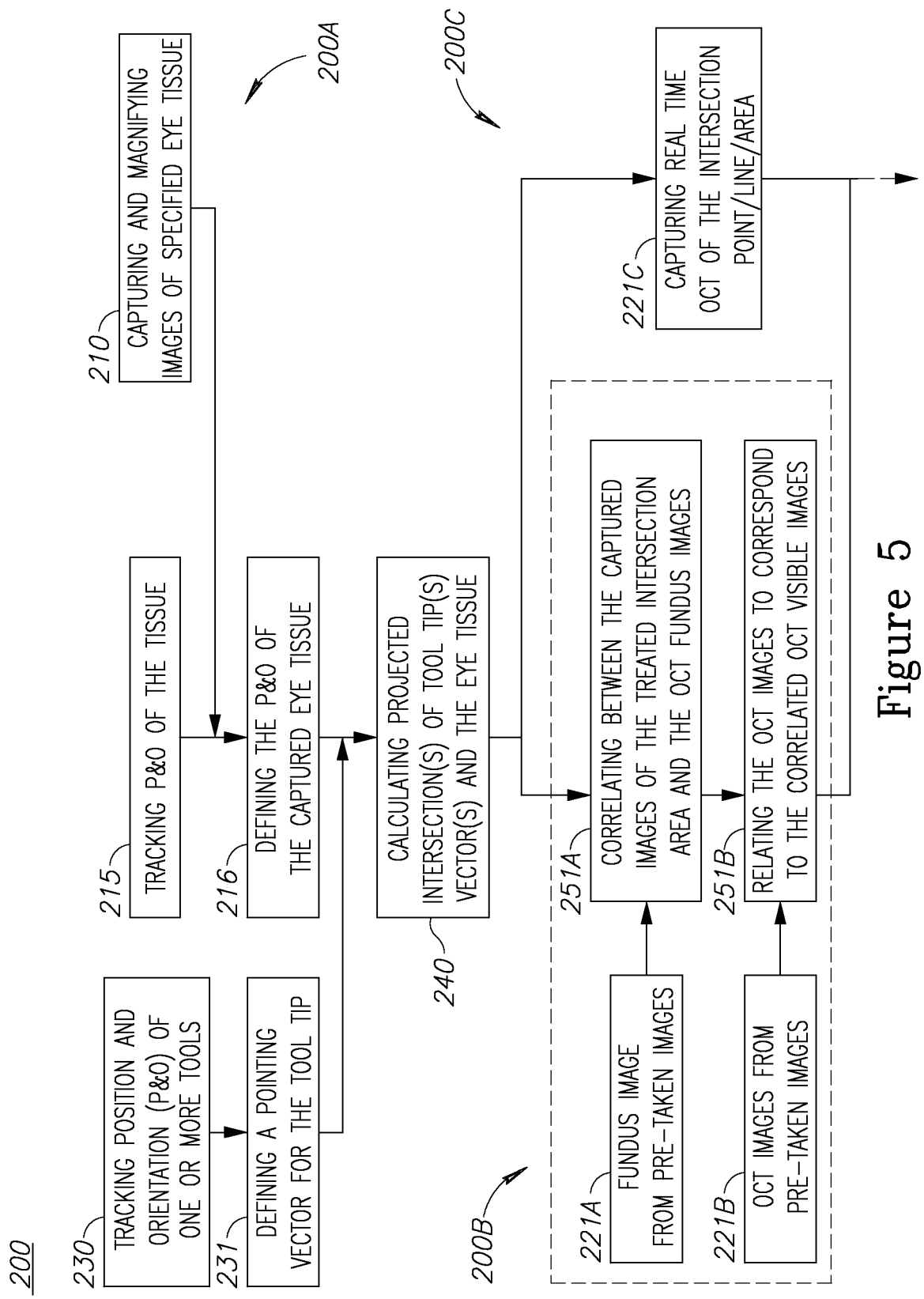

FIGS. 4 and 5 are high level flowcharts illustrating a method 200 of enhancing ophthalmological surgical procedures, according to some embodiments of the invention. As illustrated in FIG. 4, method 200 may comprise associating and displaying images by interferometric imager(s) (such as OCT imagers) with an intersection of a pointing vector with the respective tissue (stage 205). The pointing vector may be associated with a treatment tool or with any other tool or utensil, as well as with any geometrically defined direction, e.g., defined using a user interface.

Method 200 may comprise capturing and magnifying at least one image of a specified eye tissue (stage 210), optionally tracking organ movements and incorporating them into the intersection calculation (stage 212), tracking a position and orientation (P&O) of the treated eye (stage 215) (complementarily or alternatively tracking the eye by stereoscopic imaging, stage 217), tracking a P&O of at least one tool and deriving a tool tip pointing vector therefrom (stage 230), calculating an intersection between the tool tip and the specified eye tissue (stage 240), relating, spatially, at least one optical coherence tomography (OCT) image of the specified eye tissue to at least one of a tool tip location and the intersection (stage 250) (and/or to the projected intersection of the tool tip at the eye tissue), and displaying the at least one magnified image of the specified eye tissue with the at least one OCT image associated therewith according to the spatial relation (stage 260).

Alternatively or complementarily, method 200 may comprise tracking intersection(s) of pointing vector(s) with the tissue (stage 242), wherein the pointing vector(s) may be associated with any treatment tool or with any other tool or utensil, as well as with any geometrically defined direction, e.g., defined using a user interface.

Tracking eye P&O 215 may be carried out stereoscopically 217, and/or in infrared or visible light, and/or using fiducials (on the eye at captured locations), stereoscopic imaging, structured light imaging and/or gated imaging; and the specified eye tissue may be the retina of the treated eye or part thereof, with the OCT image(s) being retinal OCT images. Capturing tool P&O 230 may comprise using at least one fiducial marker for the tracking of the tool P&O (stage 232).

Method 200 may further comprise capturing one or more OCT image(s) of the specified eye tissue, e.g., retinal images (stage 220). Capturing 220 may be carried out before or during the eye treatment (stage 222). Method 200 may comprise reiterating the spatial relating during an eye treatment with updated tool tip pointing vectors and/or consecutive OCT images of the treated eye (stage 252). Capturing 220 may be carried out at least partially at the tool tip (stage 235), e.g., by an OCT imager mounted thereupon.

Displaying 260 may comprise displaying the at least one OCT image as a cross section of the specified eye tissue at the intersection (stage 265). Method 200 may further comprise calculating and displaying a 3D OCT image, derived from a plurality of the OCT images, of the specified eye tissue at the intersection (stage 270). In embodiments, the OCT images may be replaced by any other interferometrically derived 3D images (stage 272).

Spatially relating 250 the OCT images may be carried out by estimating a distance and a spatial angle of the tool tip from at least one plane of the at least one OCT retinal image. The position of the OCT retinal image(s) may be associated with the related location of the tool tip by displaying the OCT retinal image(s) at a current or at an expected intersection of the tool tip and a retina of the treated eye and/or displaying both the tool tip position and the OCT retinal image(s) in a common plane and/or providing a three dimensional reconstruction of a retinal region that is at a specified spatial relation to the tool tip, using the OCT retinal image(s).

As illustrated in FIG. 5, method 200 may comprise a method 200A comprising tracking a P&O of at least one tool and deriving a tool tip pointing vector therefrom (stage 230) and defining a pointing vector for the tool tip (stage 231); tracking the P&O of the tissue (stage 215), capturing and magnifying at least one image of the specified eye tissue (stage 210) and defining therefrom the P&O of the captured eye tissue (stage 216); and from these, calculating the intersection between the tool tip and the specified eye tissue (stage 240).

Method 200 may comprise non-realtime OCT imaging method 200B which comprises using fundus image(s) from pre-taken images (stage 221A) and correlating between the captured images of the treated intersection area and the fundus images (stage 251A); and/or using OCT images form pre-taken images (stage 221B and relating the OCT images to correspond to the correlated OCT visible images (stage 251B). In method 200B, the fundus images which are pre-taken together with the OCT images can be used to place correctly the OCT images on the captured images of the treated eye tissue, by correlating the pre-taken fundus images with the captured images of the treated eye tissue. Method 200 may comprise realtime OCT imaging method 200C comprising capturing real time OCT images of the intersection point(s), line(s) and/or area(s) stage (221C).

Consecutively, method 200 and any of methods 200A-C may comprise stages 260, 265, 270 and/or 272 as described above.

Advantageously, the disclosed invention provides the surgeon with accurately positioned OCT images which show depth details of the treated tissue, including the exact position of the tool tip within the treated tissue. The association of the OCT images with the exact location of treatment and the tool tip may be carried out in different modes, ranging from mere indication of the projected tool-tissue intersection to a 3D model of the tissue, possibly including the tool tip in the model.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A system for ophthalmological surgical procedures, the system comprising:
   at least one camera configured to capture and magnify at least one image of an eye tissue,
   a tissue position and orientation (P&O) tracker configured to track a P&O of the eye tissue,
   a tool P&O tracker configured to track a P&O of at least one tool and derive a tool tip pointing vector therefrom,
   a processing unit configured to calculate an intersection between the tool tip pointing vector and the eye tissue and to determine an association between at least one optical coherence tomography (OCT) image and the calculated intersection, wherein the at least one OCT image is generated at a region of the eye tissue surrounding the calculated intersection, wherein there is no actual contact of the tool tip with the tissue, and
   a display module configured to display the at least one magnified image of the eye tissue with the at least one OCT image.

2. The system of claim 1, wherein the eye tissue is a retina or a part of a retina, and the at least one OCT image is at least one OCT retinal image.

3. The system of claim 2, wherein the OCT images are captured at an intersection region enclosing the calculated intersection.

4. The system of claim 1, where the tissue P&O tracker is configured to track fiducials placed on external parts of the eye which are captured by the at least one camera.

5. The system of claim 1, where the tissue P&O tracker is configured to track the tissue P&O using at least one of: stereoscopic images, structured light 3D imaging and time of flight 3D imaging of the tissue.

6. The system of claim 1, wherein the tissue P&O tracker operates in infrared.

7. The system of claim 1, wherein the tool comprises at least one fiducial marker used for the derivation of the tool tip pointing vector.

8. The system of claim 1, wherein the at least one OCT image is captured prior to or during a treatment of the eye.

9. The system of claim 1, wherein the at least one OCT image is received from at least one OCT image source which is independent of the tool tip or is mounted on the tool tip.

10. The system of claim 9, wherein the at least one OCT image comprises a plurality of consecutive OCT images captured during an eye treatment, the processing unit is further configured to carry out the spatial relating repeatedly with respect to the consecutive OCT images, and the display module is configured to update the displayed OCT image and position with respect to the consecutive OCT images and the repeated spatial relating, correspondingly.

11. The system of claim 1, wherein the association of the position of the at least one OCT image with the related location of the tool tip comprises at least one of: display of the at least one OCT image at the intersection; display of the at least one OCT image at a current or at an expected intersection of the tool tip and a retina of the treated eye; a display of both the tool tip position and the at least one OCT image in a common plane; and a three dimensional reconstruction of a retinal region that is at a spatial relation to the tool tip, using the at least one OCT image.

12. The system of claim 1, wherein the processing unit and the display module are further configured, respectively, to calculate and display a 3D OCT image, derived from a plurality of the OCT images, of the eye tissue at the intersection.

13. The system of claim 1, at least partly integrated in a head mounted display (HMD).

14. A method of enhancing ophthalmological surgical procedures, the method comprising:
   capturing and magnifying at least one image of an eye tissue;
   tracking a position and orientation (P&O) of the eye tissue;
   tracking a P&O of at least one tool and deriving a tool tip pointing vector therefrom;
   calculating an intersection between the tool tip pointing vector and the specified eye tissue;
   determining an association between at least one optical coherence tomography (OCT) image and the calculated intersection, wherein the at least one OCT image is generated at a region of the eye tissue surrounding the calculated intersection, wherein there is no actual contact of the tool tip with the tissue; and
   displaying the at least one magnified image of the specified eye tissue with the at least one OCT image associated therewith.

15. The method of claim 14, further comprising capturing the at least one OCT image.

16. The method of claim 15, wherein the capturing is carried out before or during the eye treatment.

17. The method of claim 14, further comprising reiterating the spatial relating during an eye treatment with updated tool tip pointing vectors or consecutive OCT images of the eye tissue.

18. The method of claim 14, wherein the tracking of the tissue P&O is carried out using at least one of: fiducials placed on captured external parts of the eye, stereoscopic images of the tissue, structured light 3D imaging of the tissue and time of flight 3D imaging of the tissue.

19. The method of claim 14, wherein the tracking of the tissue P&O is carried out in infrared.

20. The method of claim 14, wherein the eye tissue is a retina of the treated eye or part thereof, and the at least one OCT image is of the retina or the part thereof.

21. The method of claim 14, further comprising using at least one fiducial marker for the tracking of the tool P&O.

22. The method of claim 14, wherein the displaying comprises displaying the at least one OCT image as a cross section of the eye tissue at the intersection.

23. The method of claim 14, further comprising calculating and displaying a 3D OCT image, derived from a plurality of the OCT images, of the eye tissue at the intersection.

* * * * *